United States Patent [19]
Allen et al.

[11] Patent Number: 5,488,567
[45] Date of Patent: * Jan. 30, 1996

[54] DIGITAL ANALYTE DETECTION SYSTEM

[75] Inventors: Fritz Allen, Corrales; Thomas Niemczyk, Albuquerque, both of N.M.

[73] Assignee: Acrogen, Inc., Oakland, Calif.

[*] Notice: The portion of the term of this patent subsequent to Jul. 12, 2011, has been disclaimed.

[21] Appl. No.: 243,153

[22] Filed: May 16, 1994

Related U.S. Application Data

[63] Continuation of Ser. No. 918,357, Jul. 23, 1992, Pat. No. 5,329,461.

[51] Int. Cl.$^6$ .................................................. G06G 7/75
[52] U.S. Cl. ...................... 364/497; 364/499; 364/555; 324/71.4
[58] Field of Search .................................. 364/497, 499, 364/555, 502; 324/71.4; 356/237

[56] References Cited

U.S. PATENT DOCUMENTS 5,329,461  7/1994  Allen et al. ............................. 346/497

Primary Examiner—Emanuel T. Voeltz
Assistant Examiner—Kyle J. Choi
Attorney, Agent, or Firm—Bertram I. Rowland; Bret E. Field

[57] ABSTRACT

A system and method for digitally detecting the presence of analyte particles within a sample is disclosed herein. Each analyte particle is disposed to emit an optical response upon illumination in a known manner. The digital analyte detection system includes optical apparatus for illuminating a multiplicity of distinct pixel regions within the sample so as to induce each of the analyte particles included therein to emit at least one optical response. The pixel regions are dimensioned such that the number of analyte particles included within each region is less than a maximum detection threshold proportional to variability of the optical responses.

The digital detection system further includes apparatus for measuring the emitted signal emitted from each pixel region. A data processing network receives the measurements of the emitted signals and, based on the measurements, counts the number of analyte particles within each pixel region so as to determine the number of analyte particles within the sample.

33 Claims, 7 Drawing Sheets

DIGITAL ANALYTE DETECTION SYSTEM

This is a continuation, of patent application Ser. No. 07/918,357 filed Jul. 23, 1992 now U.S. Pat. No. 5,329,461.

TECHNICAL FIELD

The technical field of this invention relates to optical methods of chemical analysis.

BACKGROUND

Chemical analysis involving the detection and quantization of light occurs in a large variety of situations. One application of this need is the detection of analytes for the determination of the presence or amount of a particular analyte. In many assays for analytes, one is concerned with either absorption or emission (e.g., fluorescence or chemiluminescence) of light. In many situations, one irradiates a sample with light and then attempts to detect the effect of the sample on the transmitted or emitted light. In the case of emitted light resulting from irradiation, non-analyte molecules may also emit light resulting in a relatively large background noise, which results in the introduction of substantial error in the measurement of the effect of the sample on the light. There are also additional systematic errors which collectively contribute to the noise associated with the measurement.

The quality of chemical measurements involving light can be defined in terms of the ratio of a suitable measure of the optical signal from a sample due to the presence of analyte to the noise variation inherent within the signal. In general, efforts to augment this signal to noise (S/N) ratio have centered on improving the sensitivity of a measurement apparatus so as to reduce the "detection limit" associated with a particular analyte. The detection limit refers to the analyte concentration within a sample above which the signal attributable to the presence of analyte is such that a desired S/N ratio is achieved. In practice, this detection limit is ascertained by conducting an experimental procedure designed to elicit an optical signal related to analyte concentration. Specifically, data relating to signal and noise intensity is plotted in the form of a calibration curve for a range of analyte concentrations, thereby enabling straightforward determination of the detection limit.

The determination of concentration in unknown samples is effected by comparing the signal obtained experimentally from the unknown with the calibration curve. A typical unit of concentration in chemical measurements is moles/liter [i.e., Molarity (M)], where a mole is defined as Avogadro's number ($6.0225 \times 10^{23}$). Unfortunately, even the most sensitive conventional experimental techniques have detection limits on the order of about one femtomolar (fM), or nearly one billion analytes per liter.

Measurements in which concentration is determined by reference to a calibration curve may be characterized as being inherently "analog" rather than "digital". That is, a signal correlated with analyte concentration is initially produced by the measurement device. The calibration curve is then consulted to obtain an approximation of the analyte concentration. Since the calibration curve may be made continuous as a function of concentration, the concentration derived from the calibration curve will generally not be an integer. In contrast, measurement data in the digital domain are often embodied in binary (i.e., two-level) signals which unequivocally represent specific integers. Accordingly, a fundamental difference between analog and digital modes of measurement is that the addition of a single additional analyte to a sample analyzed using analog means cannot be unambiguously detected. Although dramatic improvements have been made in the accuracy of chemical measurements, such advancements have been based on the fundamentally analog concepts of increasing signal and reducing noise.

In molecular samples involving low levels of analyte concentration a digital measurement methodology would afford at least two advantages: (i) reference to a calibration curve would not be required, and (ii) the addition of a single additional molecule to a sample could conceivably be detected. Such a digital technique would be of utility in samples where the analyte concentration is sufficiently low that statistical noise accompanying each binary measurement value remains less than the difference between successive integers. Accordingly, it is an object of the present invention to provide an optical technique for determining low levels of analyte concentration by means of an intrinsically digital measurement scheme.

Relevant Literature

Whitten et al., *Anal. Chem.* (1991) 63:1027–1031 describe detection of rhodamine-6G molecules by using a laser to excite fluorescence from electrodynamically levitated microdroplets.

Stevenson et al., *Applied Spectroscopy*, (1992) 46(3):407–419 discuss theoretical considerations relating to laser spectroscopic methods capable of detecting single atoms or molecules in the laser beam.

Nguyen et al., *J. Optical Society of America*, (1987) 4(2):138–143 disclose an apparatus for the detection of fluorescent species in hydrodynamically focused flows.

Tou et al., *Pattern Recognition Principles*, (1974) (ISBN 0-201-07587-3), chps. 3 and 7, discuss techniques for determining characteristic prototypes or cluster centers from a given set of data. Methods of pattern preprocessing and feature selection are also described.

SUMMARY OF THE INVENTION

A system and method for digitally detecting the presence of analyte particles within a molecular sample is disclosed herein. Each analyte particle is disposed to emit an optically detectable response upon stimulation (e.g., illumination) in a known manner. For stimulation of fluorescence as distinct from chemiluminescence, the digital analyte detection system includes optical apparatus for illuminating a multiplicity of distinct pixel regions within the sample so as to induce each of the analyte particles included therein to emit an optical signal, i.e., photons. The pixel regions are dimensioned such that the number of analyte particles included within each region is sufficiently small that the aggregate optical signal emitted by each region is less than a maximum detection threshold proportional to variability of the optical responses.

The digital detection system further includes apparatus for measuring the optical signal emitted from each pixel region. A data processing network receives the measurements of the optical signals and, based on the measurements, counts the number of analyte particles within each pixel region so as to determine the number of analyte particles within the sample.

DESCRIPTION OF THE SPECIFIC EMBODIMENTS

Apparatus and methods are provided for digitally detecting the presence of small concentrations of molecular analyte particles within a sample. As is discussed below, the term analyte particle refers to the combination of a molecular analyte of interest and a suitably homogeneous label disposed to emit light upon being stimulated. Such particles may be any entity capable of being detected, including those as small as a DNA macromolecule or a polysaccharide, or as a large as, for example, a latex particle. However, with large particles other detection techniques may be equally advantageous. The apparatus is disposed to detect low levels of emitted light from a plurality of pixel regions within the sample, where the light emitted by each pixel region is engendered by stimulation of analyte particles included therein. The emitted light is digitally analyzed so as to determine the integral number of analytes within each pixel region.

Photon emission may be achieved by irradiation of fluorophores in their absorption range, or by chemical or physical stimulation of chemiluminescent labels, which emit light upon irradiation or appropriate chemical reaction. For the most part fluorescence is more convenient and is the preferred mode. Therefore for the purpose of the description of the subject invention, fluorescence will be described. For fluorescence, the subject device will include means for irradiation of the sample to cause fluorescence. The irradiation means may not be necessary for chemiluminescence, since stimulation may be achieved by addition of a chemical reagent. Where a chemical reagent is employed, care will be taken in the measurement to relate the meausurement to the time from mixing. Alternatively, the change in rate of emission may be monitored over a predetermined time period. For the purpose of this invention, the optical signal from chemiluminescence may be equated to the optical signal from fluorescence.

For fluorescence measurements particularly, collimated light of a narrow wavelength range is directed onto each pixel region within the sample. The intensity of the emitted light will be in discrete levels in relation to the number of analyte particles present within each pixel region. The emitted light is then collected with a discrete element collector system and directed to a photodetector for quantization and analysis. A discrete element collector is an array of discrete optical elements arranged to refract or reflect light from the sample point into a quasi-collimated beam. An example of such a collector is a low f-number Fresnel lens/reflector array of the type produced by 3M Corporation (Minneapolis, Minn.).

Figure 1:
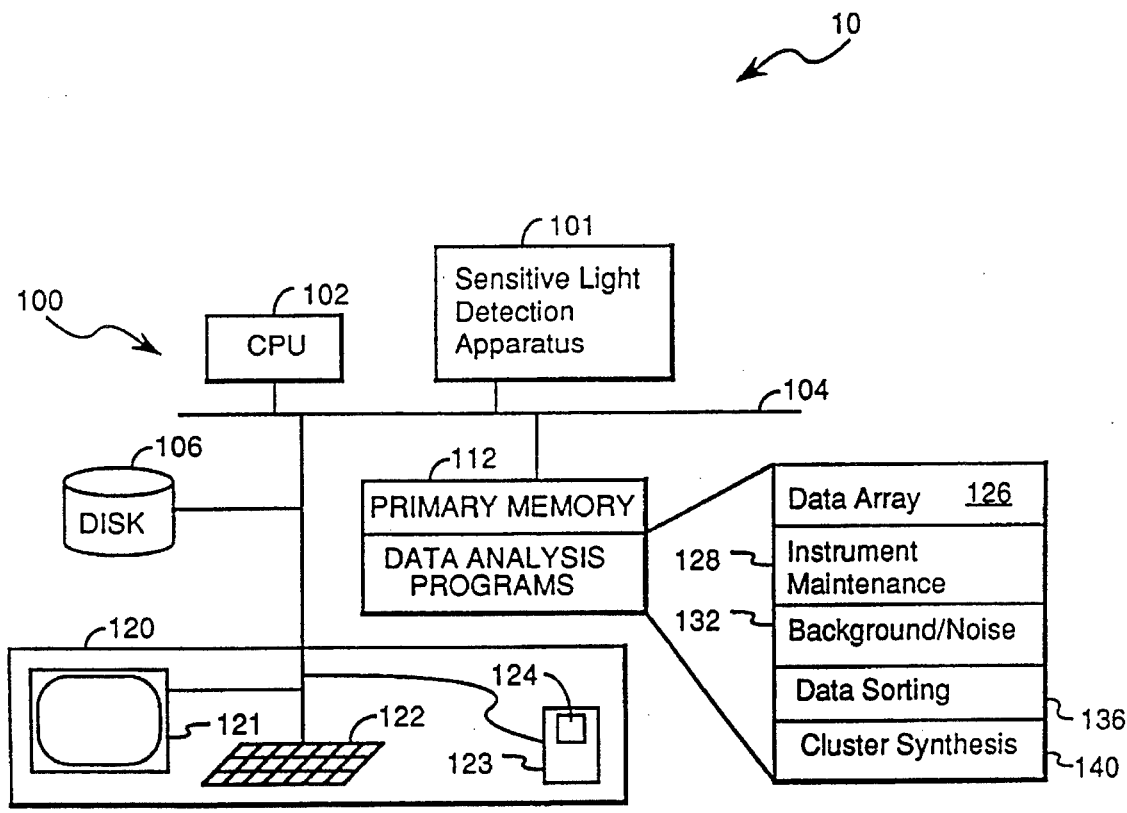
FIG. 1 is a block diagrammatic representation of a preferred embodiment of the digital molecular analyte detection system of the present invention.

Referring to FIG. 1, a preferred embodiment of the digital analyte detection system 10 of the present invention includes a general purpose computer system 100 operative to analyze measurement data accumulated by a sensitive light detection apparatus 101. The computer system 100 includes a central processing unit 102 that is interconnected by a system bus 104 to secondary memory 106 (e.g., a magnetic disk storage device), to primary memory 112 (i.e., high speed, random access memory), and to one or more user interfaces 120. Each user interface 120 typically includes a display or monitor 121, a keyboard 122, and a mouse pointer device 123 with item selection button 124.

Stored in primary memory 112 are a data array 126 as well as a variety of computer programs (software) used to implement the digital detection method of the present invention. Included among the software contained in primary memory 112 is an instrument maintenance program 128 for controlling the light detection apparatus 101. Also stored in primary memory 112 are a number of data analysis programs described in detail below. Specifically, an inventive data clustering scheme facilitating detection of analyte particles comprises a background/noise threshold routine 132, a data sorting routine 136, and a cluster synthesis routine 140.

The sensitive light detection apparatus 101 will typically include an optical system substantially similar to that described in, for example, copending U.S. patent application, Ser. No. 07/855565, filed Mar. 23, 1992, and entitled SENSITIVE LIGHT DETECTION SYSTEM, which is herein incorporated by reference. As mentioned above, the apparatus 101 is operative to illuminate a plurality of pixel regions within a sample of analyte particles in order to induce fluorescence of the analyte particles within each region. The light (optical response) emitted by each analyte particle upon illumination at known intensity for a predetermined time is directed to a detector operative to generate an electrical detection signal in response thereto. The magnitude of the detection signal corresponding to each pixel region is then stored in data array 126.

Figure 2:
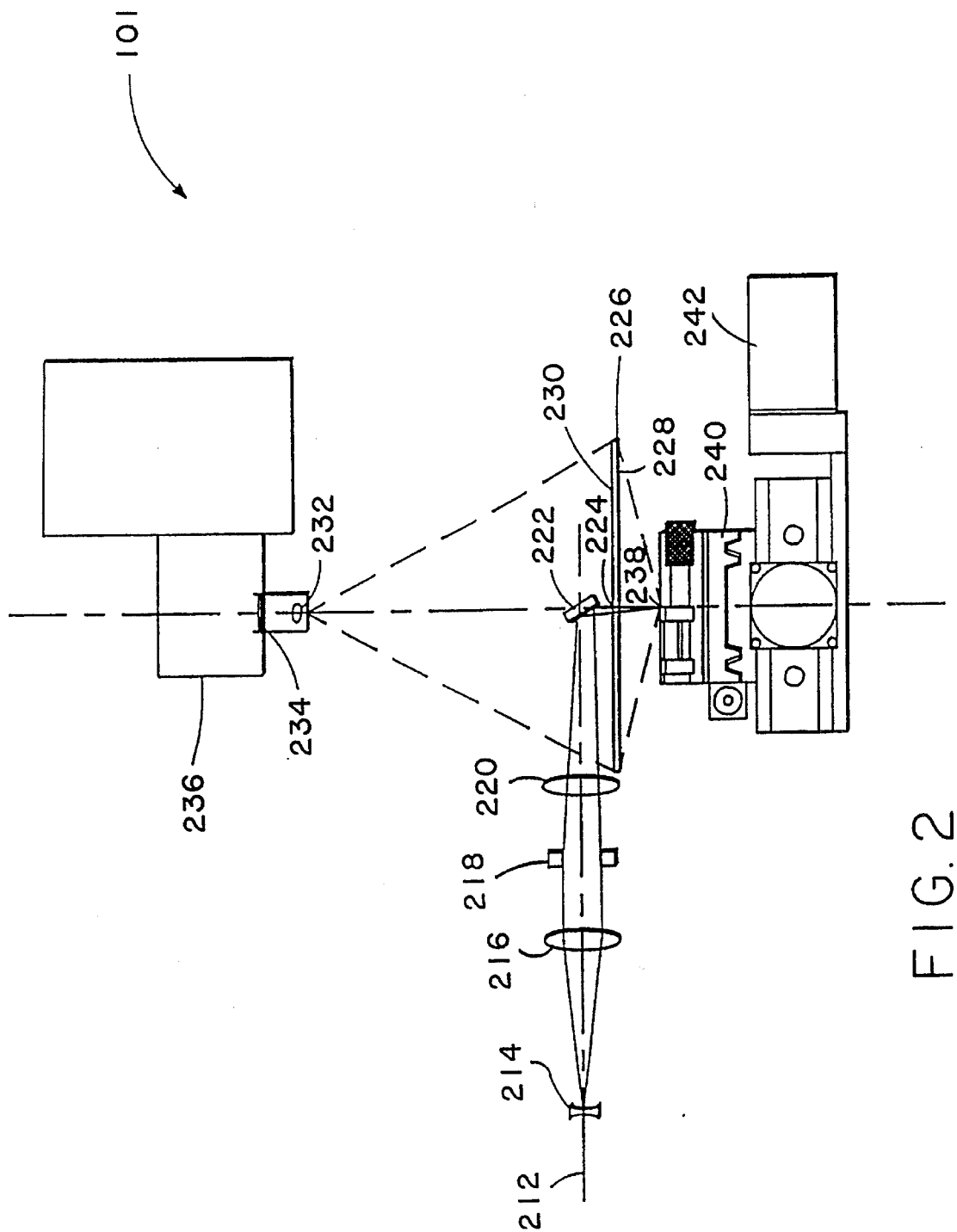
FIG. 2 shows a diagrammatic elevational view of a preferred implementation of a sensitive light detection apparatus incorporated within the inventive detection system.

FIG. 2 shows a diagrammatic elevational view of a preferred implementation of the sensitive light detection apparatus 101. The apparatus 101 has a laser beam 212 which is passed through a first lens 214 which expands the laser beam and directs the beam to second lens 216 where the beam is recollimated. The collimated beam is then passed through an adjustable aperture 218 to define the diameter of the beam and finally through focusing lens 220. Focusing lens 220 is mounted on a stage, not shown, where focusing lens 220 may be moved along the optical axis, so as to change the beam diameter as it is incident on the sample. The laser beam 212 exits the focusing lens 220 and is reflected by a first surface mirror 222. The light then passes through a hole 224 in discrete element collection system 226, which comprises a first discrete element collector lens 228 for collecting the emitted light and a second discrete element collector lens 230 for focusing the light. Usually, the focal length of the first discrete element collector lens, which will have a structure analogous to a Fresnel lens, will be substantially less than the focal length of the second lens (which may or may not be a Fresnel lens), generally being less than about 60% of the focal length of the second lens. The collection angle for the first discrete element collector lens will usually be at least about 90° for direct emission. The emitted focused light will then be transmitted to a second lens 232 and directed to a filter pack 234, which serves to exclude light outside of the wavelength range of the light emitted from the fluorophore label within each analyte particle. The filter pack may be implemented to effect wavelength isolation by using, for example, conventional optical filters, monochromators or time-gating techniques. The light of the desired wavelength is then detected by a photomultiplier tube and preamplifier 236 for transmission to electronic circuitry for analysis.

Figure 3:
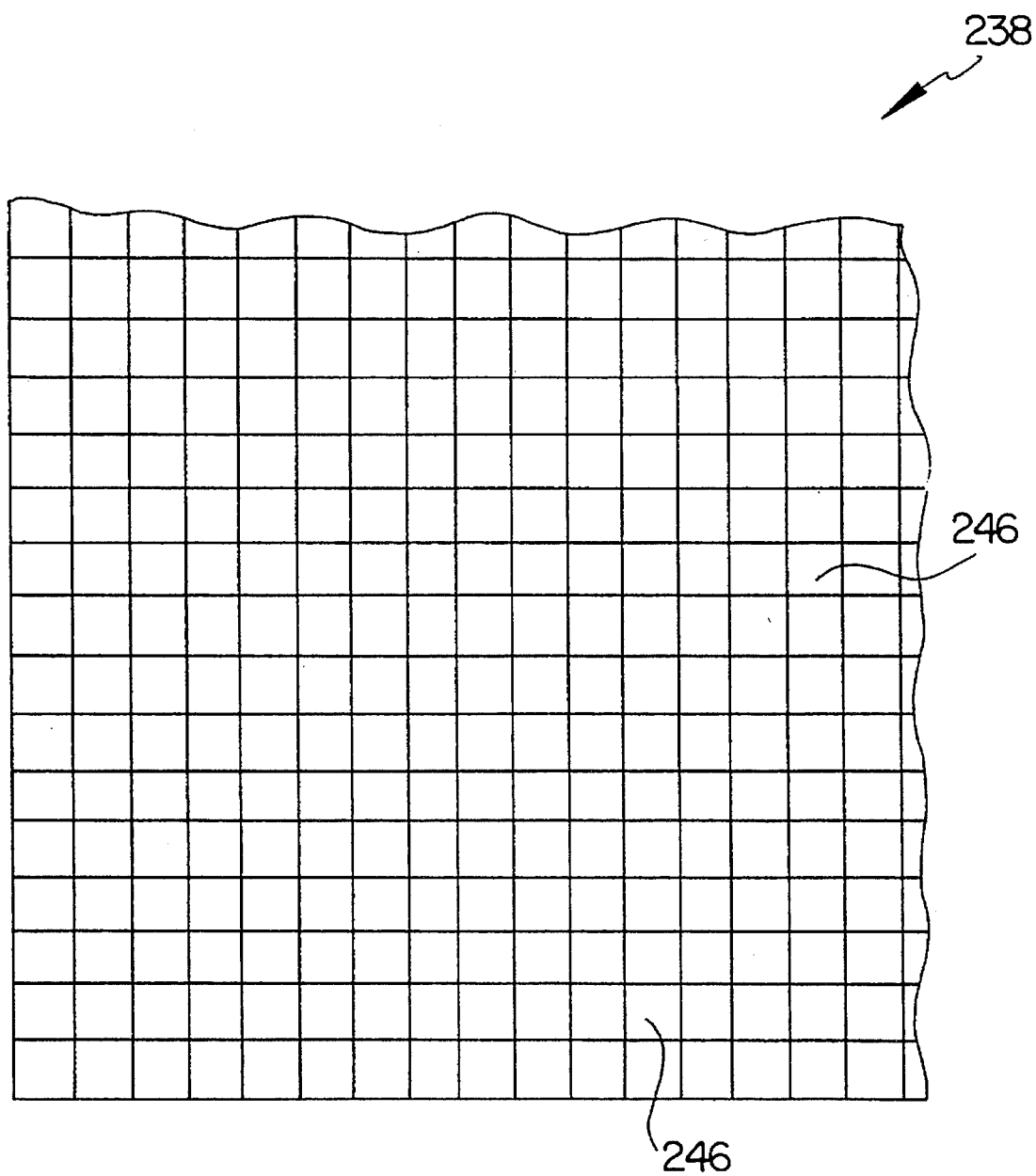
FIG. 3 depicts the manner in which a sample to be analyzed is divided into a two-dimensional array of contiguous pixel regions.

The sample 238 is supported by X-Y stage 240, which allows the incident light to illuminate each pixel region included therein. As is shown in FIG. 3 and is described more fully below, the sample 238 will preferably be divided into a two-dimensional array of contiguous pixel regions 246. The pixel regions 246 will be selected to be small enough so that generally less than a desired number (e.g., two) of analyte particles will be present within each pixel region. For example, the volume of sample to be analyzed may be selected such that there exist approximately five pixel regions for each analyte particle. Such a ratio nearly ensures that the aggregate fluorescent energy (emitted signal) engendered by analyte particles within each pixel region will be sufficiently small that the statistical variation therein remains less than the optical response of a single analyte particle. However, if less than absolute precision may be tolerated a sample volume may be selected which results in a smaller ratio of pixel regions to analyte particles. The number of analyte particles within a given pixel region is determined by finding the integer nearest the ratio of the emitted signal collected from the pixel region to one optical response. This set of integers is stored in data array 126, and may be summed to enable a digital determination of the number of analyte particles within the sample 238. A stepper motor 242 (FIG. 2) is provided for accurate movement of the sample 238 in the X and Y directions as directed by the instrument maintenance program 128.

The X-Y stage 240 may be assembled from, for example, a Newport model 405 dual-axis translation stage. Appropriate modification would entail accommodation of a 20 turn per inch lead screw fabricated from ¼ inch — 20 stock stainless steel threaded rod. Use of two stepper motors provides 3.175 microns of linear travel per step for both the X and Y axis. Total travel for X and Y is limited to about one half inch. Limit switches at each axis end provide a means of centering the stage. This establishes a known reference x,y of 0,0. Image scanning of the sample can then be performed for pixel regions having lateral dimensions on the order of 3.175 microns.

Figure 4:
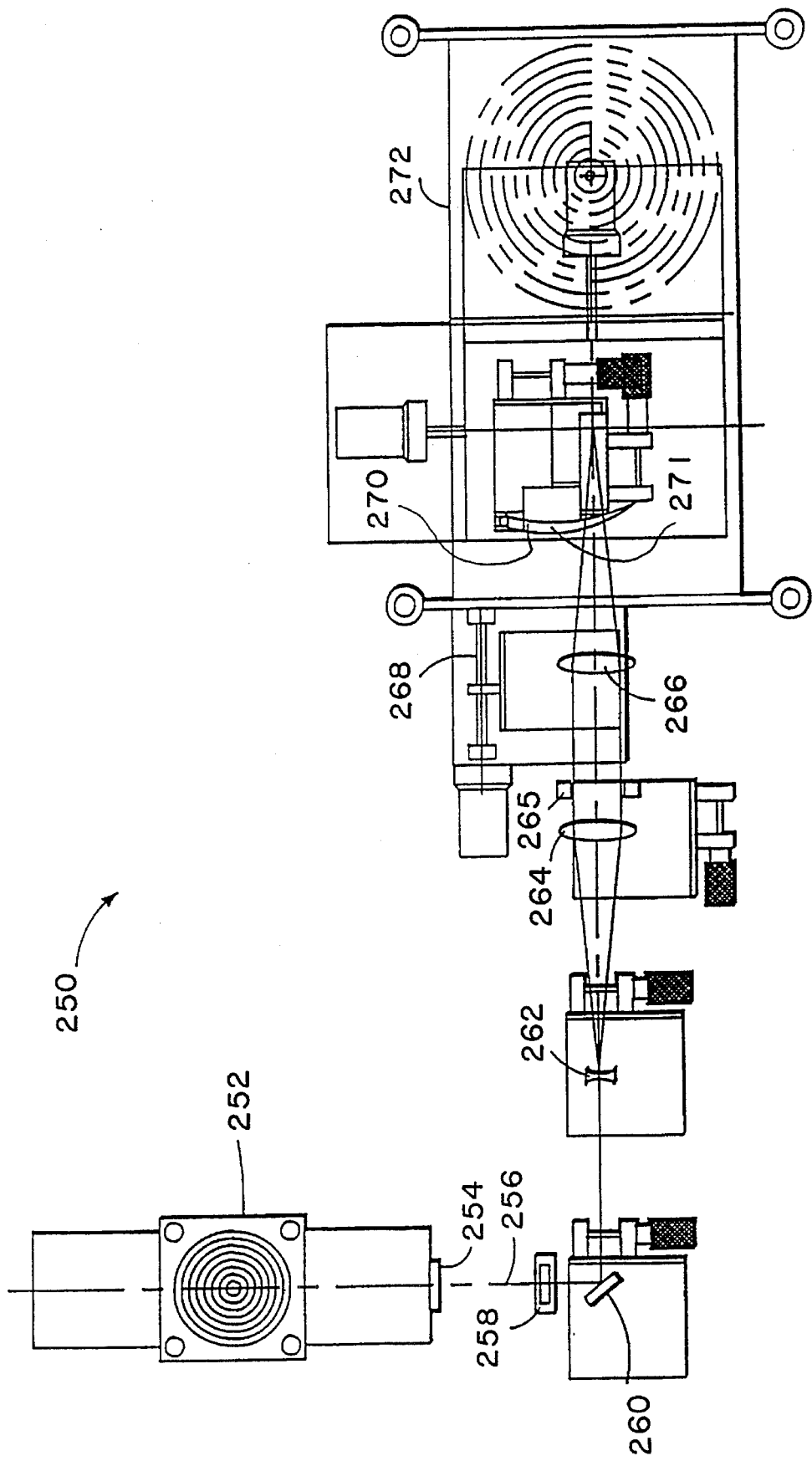
FIG. 4 is a plan view of a first alternative implementation of the sensitive light detection apparatus.

In FIG. 4, a first alternative implementation 250 of the light detection apparatus is shown diagrammatically with a laser source 252 fitted with beam shutter 254. The laser beam 256 is directed through a line filter 258 and then is reflected by turning mirror 260 into the lens system comprising an expanding lens 262, a collimating lens 264, an adjustable aperture 265, and a focusing lens 266 which is mounted on a stepper driven stage 268. A sample stepper stage 270 is provided to support and move the sample per instruction of instrument maintenance program 128, holding the sample in place with slide holder 271, which is positioned under moveable discrete element collector system 272 (shown displaced from operational position directly above the sample).

For the most part, the light source will be a laser, where the intensity of the beam may vary from a power rating of 1 μW to about 100 mW. The light wavelength may be varied widely, depending upon the absorption characteristics of the fluorescent label included within each analyte particle. For the most part, the light will be at a wavelength above 350 nm, usually about 400 nm, and usually below 700 nm, more usually below about 550 nm. Desirably, each analyte particle will include a fluorescer providing for a large Stokes shift, usually at least about 20 nm, preferably at least about 50 nm.

For varying the beam size, one may use a movable lens, which by varying the distance from the sample will change the beam size. By employing appropriate stepper motors, one can provide for smaller or greater changes in the beam with each step.

The light which is emitted from each pixel region 246 is then efficiently collected using a discrete element collector system which provides for the collection of the light and its transmission to a photodetector. The discrete element collector system will usually be a multi-lens system, where the collector lens, proximal to the sample, will generally have a low f-number, usually less than about 2 and greater than about 0.05, generally being in the range of about 0.075 to 1.0. The low f-number discrete element collectors do not normally produce a high quality collimated beam. However, by employing a second lens of about the same diameter and a larger f-number, usually greater than 0.5, generally from about 1 to 10, the light may be focused on the detector. The discrete element collector lens and the second lens, will generally have a separation of from about 0 to 50 cm, usually being in close proximity of from about 0.1 to 5 cm. The discrete element collector lens will usually be at least about 1 cm$^2$ and may be as large as about $1 \times 10^4$ cm$^2$, usually not greater than about 500 cm$^2$ in area.

By including a perfect spherical reflector behind the emitter to reflect the light going away from the detector back through the source and into the discrete element collector system, the fraction of solid angle collected into the collimated beam emergent from the discrete element collector system can be doubled. The spherical reflector must be placed one sphere radius away from the source and on the opposite side of the emitter from the discrete element collector. For pixel regions of area A, the spherical reflector radius should be on the order of 10 times A, or greater, in order to cause the source to remain point-like relative to the reflector. If this is not the case, larger portions of the light will not be reflected back into the lens.

The solid angle of light which will be collected can be calculated based on the collection system employed.

By using the above system the solid angle fraction collected in a system with an ideal collector can be as high as 0.90, while more realistically with f-numbers for the discrete element collector varying from 0.5 to 0.05, estimated solid angle fractions will be in the range of about 0.26 to 0.81.

Figure 5:
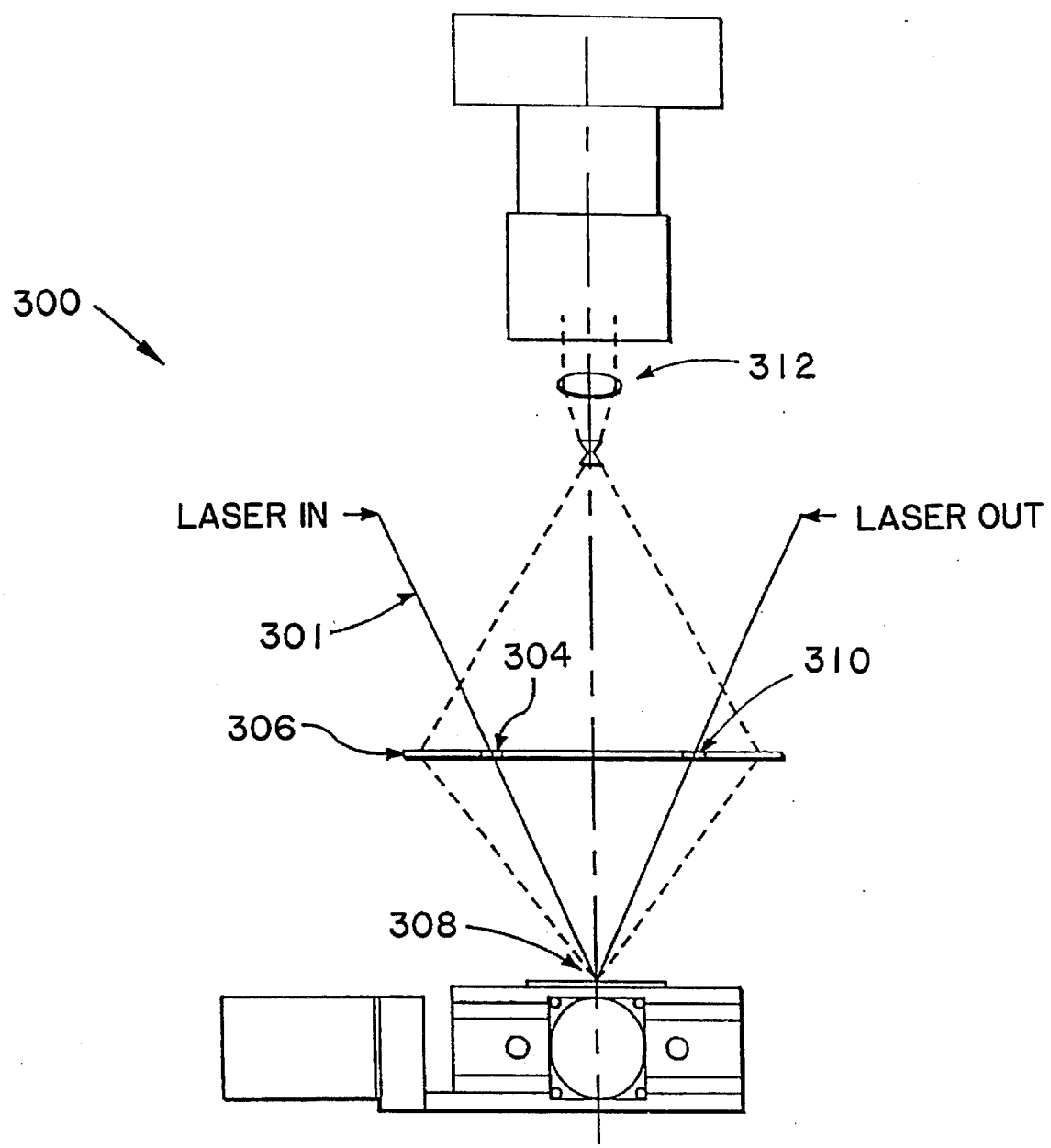
FIG. 5 is a plan view of a second alternative implementation of the sensitive light detection apparatus.

In a second alternative implementation of the sensitive light detection system generally indicated by reference numeral 300 in FIG. 5, instead of having the light incident to the sample being at right angles to the sample, the incident light is at other than normal to the sample. In FIG. 5, a laser beam 301, which has been processed as described in FIG. 2, is reflected by a reflecting mirror (not shown) so as to pass through hole 304 in discrete element collector system 306. The light strikes the sample 308 and is reflected from the sample through hole 310 and then discarded by any convenient means. The emitted light from the sample 308 is focused by discrete element collector system 306 and directed to lens 312 to be processed as previously described in FIG. 2.

Figure 6:
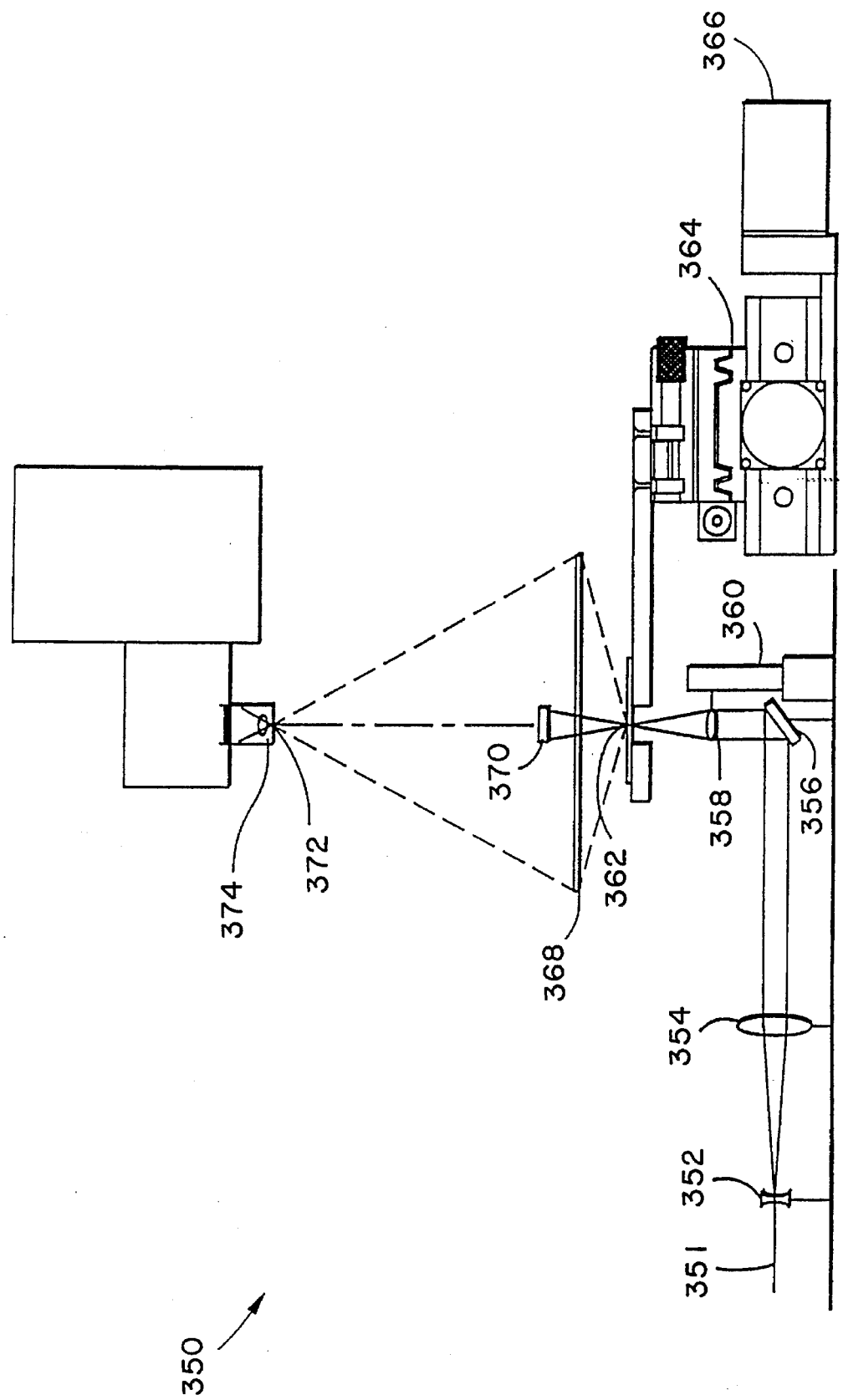
FIG. 6 depicts a third alternative implementation of the sensitive light detection apparatus.

In a third alternative implementation of the sensitive light detection system generally indicated by reference numeral 350 in FIG. 6, instead of having the light incident to the sample originating above the sample and passing through holes in the discrete element collector system, the sample is mounted on a transparent substrate and the incident light strikes the sample from below. In FIG. 6, a laser beam 351 is expanded through a first lens 352, which expands the laser beam and directs it to a second lens 354 where the beam is recollimated. The collimated beam is reflected by a first surface mirror 356 and directed to a focusing lens 358 mounted on an adjustable stage 360 which allows the beam to be focussed at the sample plane. The sample 362 is supported by X-Y stage 364 which allows each pixel region of the sample to be separately illuminated by the incident light. A stepper motor 366 is provided for accurate movement of the sample 362 in the X and Y directions per instructions issued by instrument maintenance program 128.

Unabsorbed excitation light passes through the discrete element collector system 368 and is absorbed by the long pass filter 370. Alternatively, the long pass filter may be replaced by a dichroic mirror placed at a 45° angle to the unabsorbed incident beam and reflecting the beam away from the detector where the light beam can be discarded by any convenient means.

The emitted light from the sample 362 is focussed by the discrete element collector system 368 and directed through spatial aperture 372 and to collector lens 374 to be processed as previously described in FIG. 2.

Analyte Particle Characteristics

The digital detection technique of the present invention can be used for detecting a wide variety of analytes employing emission spectroscopy, where emitted light is the detected signal. While emitted light may be as a result of, for example, fluorescence, chemiluminescence, or phosphorescence, the term "optical response" as employed herein is intended to collectively refer to the light emission from a single analyte, however induced. In addition, the term "emitted signal" as used herein corresponds to a measurement of the optical responses detected from a particular pixel region. The sample will preferably be a solid sample in which detectable label not bound to an analyte may be removed through a conventional washing procedure. In addition, the sample assay will be uniform in order to ensure that each analyte particle elicits a substantially identical optical response subsequent to being exposed to equal illumination energy.

In a preferred embodiment the analyte particles within each pixel region are measured individually based on discrete signal units providing optical responses substantially above a background noise level. The magnitude of each optical response is required to be large enough to allow the particular photodetection apparatus employed to discriminate between optical responses and ambient background noise. One or more optical responses of a signal unit may be associated with a signal analyte particle, but the number of units will be low and substantially identical for each analyte particle. For the most part, the number of signal units per analyte particle will be one. A signal unit within any given analyte particle could be a fluorescent particle or fluorescer intercalated DNA molecule of known fluorescence and capable of reproducible production. The analyte included within the analyte particle could be a single molecule or an aggregation.

The assay medium will have low concentrations of analyte, generally at picomolar or less, frequently femtomolar or less. Assay volumes will usually be less than about 100 μl, frequently less than 10 μl and may be 1 μl or less. Each pixel region 246 (FIG. 3) will generally be not greater than 100 um$^2$, usually not greater than about 50 um$^2$ and may, as mentioned above, be as low as 10 um$^2$. The size of each pixel region 246 will depend on the concentration of the analyte, the rate at which it is desired to process each sample 238, the ease with which individual optical responses may be discriminated, and the like.

The assays will normally involve specific binding pairs, where by specific binding pairs it is intended that a molecule has a complementary molecule, where the binding of the members of the specific binding pair is at a substantially higher affinity than random complex formation. Thus, specific binding pairs may involve haptens and antigens (referred to as "ligands") and complementary binding members, such as antibodies, enzymes, surface membrane protein receptors, lectins, etc. (generally known as "receptors") and nucleic acid sequences, both naturally occurring and synthetic, either RNA or DNA, where for convenience nucleic acids will be included within the concept of specific binding members comprising ligands and receptors.

In carrying out the assay, there will normally be involved a conjugate of a specific binding member and a detectable label. As already indicated, a fluorescent label will be preferred, but other discrete labels which may be detected include chemiluminescent labels. Methods of preparing these conjugates are well known in the literature. Depending upon the analyte, various protocols may be employed, which may be associated with commercially available reagents or such reagents which may be modified.

Data Acquisition Using Sensitive Light Detection System

As noted above, a detailed discussion of the manner in which optical responses from each pixel region within a particular sample may be collected and quantized by the sensitive light detection apparatus is provided in aforementioned copending U.S. patent application, Ser. No. 07/855565. Nonetheless, in order to facilitate explanation of the digital detection technique of the present invention, preferred implementations of the computer, electronics and software utilized by the light detection system to acquire emitted signal data are set forth below:

Electronics

Subsequent to separation of the laser illumination from the optical response energy using conventional optical filtering techniques, the optical responses will typically be detected using a photomultiplier tube (PMT). The PMT used is the Hamamatsu 1477 one inch side on tube. The tube is constructed with a multialkali photo-cathode with a UV glass window and has a photon to electron gain on the order of $5.3 \times 10^6$ at an anode to cathode potential difference of 1000 volts.

The current output of the PMT is directly coupled to the pulse generator circuit disposed to operate in a digital mode. In digital mode operation single electronic pulses are counted as single photon events. This mode, also known as the photon counting mode, is only possible at low levels of light where photons are generally spaced far enough apart to prevent dc biasing. It is assumed that the dimensions of each pixel region are chosen to be sufficiently small that such dc biasing, which tends to accompany higher intensity optical response energy, does not occur.

The circuit converts the current from the tube into a voltage level, compares the voltage value against a threshold discriminator value, and generates a pulse to the remote counter circuit. Each pulse to the counter is then counted as a single photon event.

A pair of operational amplifiers comprise the preamp portion of the pulse generator circuit. The preamp portion converts current pulses around a micro-ampere into a voltage pulse of approximately 1.0 volt. A comparator is used as a discriminator to detect when these pulses are greater than a preset value. When the pulses are greater than this discriminating level, a logic transition occurs and a pulse shaper circuit converts this into a defined 10 nsec pulse.

The computer interface consists of circuitry to convert the PC computer instructions into logical commands and status information into computer logic. This interface is built on a full size card for a PC slot. The basic components on the card are the bus transceiver, address decoders, function latches, line receiver, and counter circuits.

The computer interface uses 8 I/O port addresses, hex 0310 to 0317. Reads from ports 0310 to 0312 provide 20 bits from the counters. When the counters are gated by the timer circuit, with a write to 0317, pulses received by the line receiver are counted for the defined gate period. The gate period is programmed by writes to locations 0310 to 0312.

The 20 bits of counts provide capability to greater than 1 million. Additional bit patterns written to ports 0313 to 0315 provide control of laser shutter, high voltage power supply, the three axes (i.e., X, Y and Z) stepper motors, and the operating mode of the timer circuit and the remote pulse generator. A read from 0313 provides information regarding the three axis limit switches.

The motor driven board accepts logic signals from the computer interface and translates them into position commands. For incident illumination on the order of 0.1 to 1.0 mW, the motor driven board will cause each pixel region to be illuminated for dwell times of approximately 1 to 100 msec. For illumination of between 10 and 100 mW, pixel dwell times typically range from 10 to 100 μsec. Logic lines for each axis provide motor enable, direction, step size, and the step pulse. Limit switches at the X, Y and Z axis ends are delivered to the computer interface and also wired to protection circuitry. The protection circuitry prevents the stepping of the motors when the limits have been reached in the event that computer instructions fail to detect the limit.

Computer

A PC compatible computer is used to control the instrument, make the measurements, and perform the analysis and imaging. A printer and color plotter are attached for hard copy outputs.

The computer motherboard is equipped with an INTEL® 80286 microprocessor and 80287 math coprocessor which together comprise the CPU 102 (FIG. 1). The motherboard further includes a 1024 Kbyte memory, keyboard and speaker connections, and 8 expansion slots.

An AST ADVANTAGE® multifunction board provides 576 Kbytes of primary memory 112 (FIG. 1), one serial port for the plotter, and one parallel port for the printer. An IBM® hard/floppy disk controller board and external floppy disk driver board provide communication links to the disk storage media 106. A VIDEO SEVEN VEGA VGA® board provides high resolution graphic capability up to 800×600 pixels.

Of the three board slots remaining, one is used by a custom developed circuit card for control and monitoring of the instrument and two slots are available for expansion. The custom board is the computer interface board discussed in the electronic section. It provides the means of controlling the instrument data collection.

Software

Data collection software included within the instrument maintenance program 128 (FIG. 1) has been developed using the C programming language. It was compiled with the MICROSOFT® C compiler version 5.1 and linked with libraries from MICROSOFT® and VERMONT CREATIVE SOFTWARE®. It is a window oriented package with several levels for data collection and maintenance operations. Data files written to the 3.5 inch drive include a binary FCD file containing header information, operating parameters, and the data. Also written are .GRD files for 3-D image plotting of photon count data as a function of pixel region, .DAT files containing X and Y coordinates and photon count data, and .COR files with just coordinates.

The .DAT file can be used to provide a .GRD file that uses smoothing factors for interpolation of missing data points. The .COR file can be used to re-image at the same locations as a previous run.

The graphic software is written in C and linked with the GSS Graphic libraries. This provides a visual display of the data collected and capability of sending the display to the color plotter.

The GOLDEN SURFER® software package is a commercial product that does the 3-D surface imaging and 2-D topographical views. There are six programs, GRID, SURF, TOPO, VIEW, PLOTCALL, and PLOT. GRID reads data files containing the photon counts (emitted signal data) from each pixel region and provides the means to generate a grid image of the data. The output from this program can be read by SURF for 3-D imaging or by TOPO for 2-D contours. PLOTCALL and PLOT provide the means to output these views to the color plotter. VIEW is a utility that displays the plotter generated files on the screen and provides zoom and pan functions.

The LOTUS 123® spreadsheet software package is also used in analysis of data. Data that is not normally collected automatically by the instrument can be processed and displayed by the graphic functions. Other scientific processing can also be applied to data collected by the instrument, such as applying photon pulse pile up correlation equations to the actual data.

Compilation and Analysis of Pixel Data

The inventive digital detection system 100 is designed to operate in one of two modes to determine the number of analyte particles within the sample represented by the pixel data included within the array 126. Again, the value stored within an arbitrary element of the array 126 corresponds to the magnitude of the emitted signal collected from a particular pixel region within the sample. Specifically, the system 100 is designed to operate in a first, or "direct-counting" mode upon specification by a user that the size of the label included within each analyte particle is less than the area of the pixel regions 246. When the label size exceeds the area of the pixel regions the system 100 operates in a second, or "pixel-clustering", mode.

I. Direct Counting

In the direct-counting mode the magnitude of the emitted signal from each pixel region 246 is compared with a background intensity characteristic of the sample. In pixel regions wherein the emitted signal thereof exceeds the background intensity by the response of an individual label, the number of analyte particles may be counted by dividing the emitted signal (less background) by the magnitude of the label. This is effected by comparing each value stored within the array 126 with a detection threshold proportional to the sum of the sample background intensity and the magnitude of label within each analyte particle. Those data values less than the detection threshold will then generally be ignored, while the values of the remaining elements within the array 126 are normalized by subtracting the background intensity of the sample. Each normalized entry within the array 126 is then divided by the magnitude of the label response and rounded to the nearest integer, with the number of analyte particles within the sample being determined by summing the results of each division. A suitable method for calculating the ambient background intensity of the sample is included below in the description of the pixel-clustering mode.

Since in the direct-counting mode the anticipated analyte particle concentration will often be sufficiently low that each pixel region is selected to be appreciably larger than the size of individual particles, it is relatively unlikely that an analyte particle will be located on the boundary between adjacent pixel regions. Nonetheless, in such instances the possibility exists that the particle will not be detected, since the energy contributed thereby to the emitted signal associated with the adjacent pixel region may be insufficient to render either signal larger than the detection threshold. In applications requiring extreme precision it may be desired to account for this relatively unlikely possibility. One technique designed to facilitate detection of analyte particles positioned on pixel boundaries involves shifting the orientation of the pixel array 238 relative to the sample and collecting a second set of data. In particular, the array would preferably be translated relative to the sample by approximately one-quarter pixel dimension in the X and Y directions. Data based on the emitted signal from each pixel region would again be collected, and a second count of the number of analyte particles would be performed as described above. If in the first count an analyte particle were positioned on a pixel boundary and went undetected, the second count will exceed the first. Likewise, if the second count turns out to be less than the first it is probable that the pixel boundaries were shifted so as to overlap an analyte particle detected during the first count. In either case the larger count is indicative of the number of analyte particles within the sample.

II. Pixel Clustering

As noted above, the detection system 100 is disposed to operate in the pixel-clustering mode upon specification by a user that the area of the pixel regions 246 are less than the size of individual analyte particles. As a consequence, the pixel regions among which an individual particle is distributed must be incorporated into a single entity, or "clustered", to enable an accurate determination of the number of analyte particles within the sample. As is described in detail below, the clustering process is commenced by separating the emitted signal data collected from each pixel into a set of background data and into a set of pixel data representative of image elements of interest. The signal values within the data set of interest are then arranged in descending order of magnitude (brightness). The largest data value is designated as the nucleus of a first pixel cluster, and pixels of interest which are sufficiently near the first nucleus are incorporated into the first pixel cluster. The criterion for "nearness" may be modified on the basis of, for example, the shape of the analyte particles or the specific goals of the detection process. The pixel values grouped into the first cluster are deleted from the list of interesting pixel values, and the largest of the remaining values is designated as the nucleus of a second pixel cluster. This process is repeated until a predefined percentage of the pixels of interest are grouped into clusters. A Fortran computer program written to implement the pixel clustering scheme of the present invention will be described with reference to the flow chart of FIG. 7.

Figure 7:
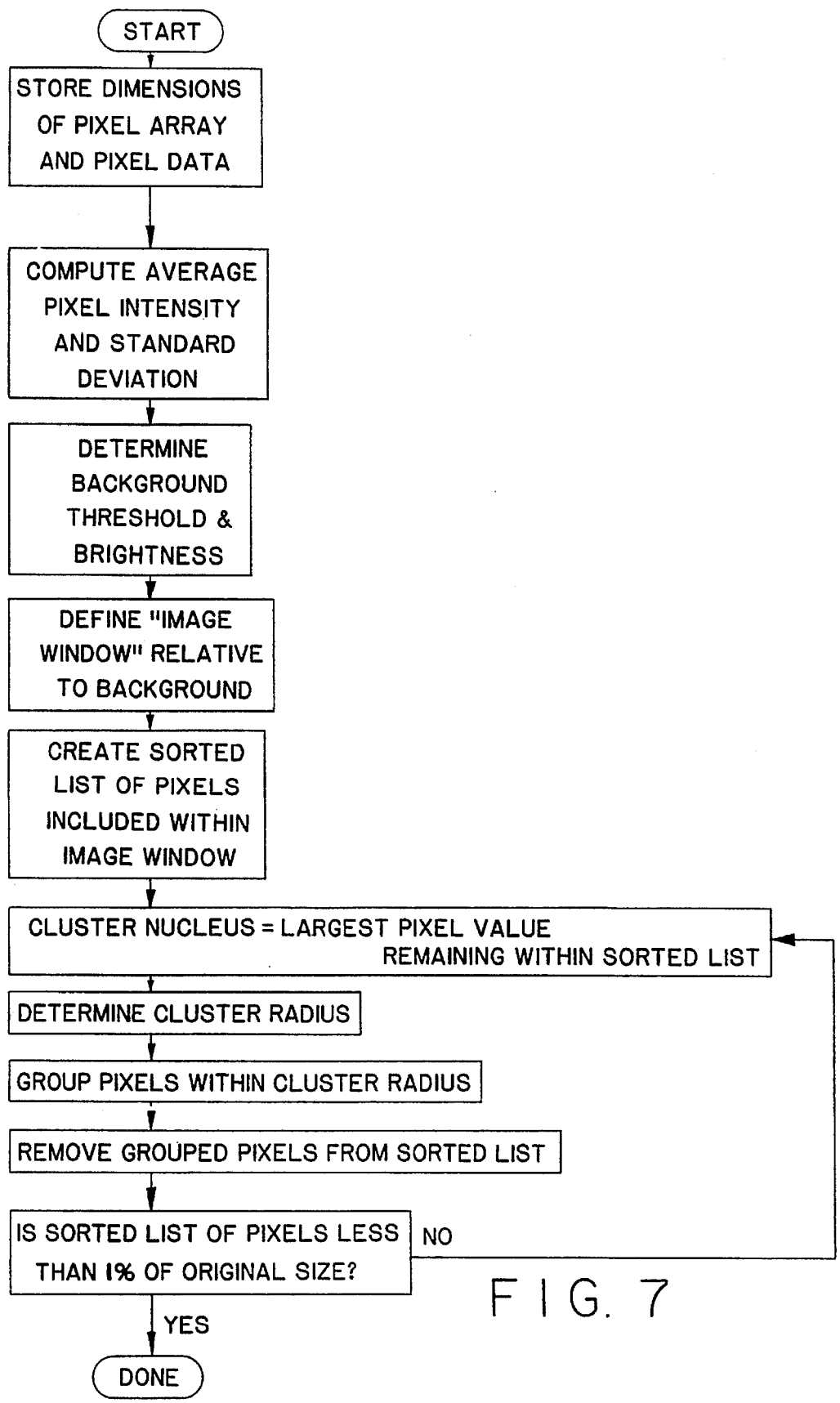
FIG. 7 is a flow chart representative of the pixel clustering process utilized in the digital detection scheme of the present invention.

As shown in FIG. 7, the clustering program is initiated by reading into a data file the dimensions of, and values stored within, the pixel data array 128. The dimensions of the array 128 in the X and Y directions are respectively denoted as Nx and Ny. The pixel values and the square of the pixel values read in from the array are then separately summed and respectively stored as integers SUM1 and SUMSQ1. SUM1 is divided by the product of Nx and Ny (i.e., by the number of entries within array 128) in order to determine the average ($AVE_1$) pixel intensity of all of the elements within the array 128. In addition, the standard deviation ($\sigma_1$) of the set of pixel data is determined in accordance with the expression:

$$\sigma_1 = \{(SUMSQ1-(SUM1)_2/(NxNy))/(NxNy-1)\}^{1/2} \quad [1]$$

The parameters $\sigma_1$ and $AVE_1$ are utilized to determine the background threshold referred to in FIG. 7. Specifically, the background threshold is denoted by the value TEST and is given by:

$$TEST = AVE_1 + 2.5\,\sigma_1 \quad [2]$$

Each pixel data value is compared with TEST, with the sum of those values less than TEST being identified by SUM2 and the sum of the squares of values less than TEST corresponding to SUMSQ2. A revised average pixel intensity $AVE_2$ is then computed:

$$AVE_2 = SUM2/N \quad [3]$$

wherein N corresponds to the number of pixel values less than TEST. In this way $AVE_2$ is more characteristic of the background brightness than is $AVE_1$ in that relatively bright features are not included within the SUM2 term of equation [3]. A revised standard deviation, $\sigma_2$, is then calculated as:

$$\sigma_2 = \{(SUMSQ2-(SUM2)_2/(N^2))/(N^2-1)\}^{1/2} \quad [4]$$

Based on the revised approximation of the background brightness $AVE_2$ and revised standard deviation $\sigma_2$, an image window encompassing pixel values corresponding to emitted signals of interest is defined relative to the background brightness. A lower boundary WINLO of the image window will preferably exceed the background brightness by five standard deviations, and hence is defined by:

$$WINLO = AVE_2 + 5\sigma_2 \quad [5]$$

An upper boundary WINHI of the image window will generally be fixed at the magnitude of the largest pixel value. The set of pixel values of interest is then searched and those having magnitudes within the image window are sorted in descending order of magnitude (brightness). The number of pixel values in this sorted list is denoted by NOUT, with the X and Y coordinates of the sorted pixel values being stored in pointer arrays INDX and INDY, respectively. Specifically, the X and Y coordinates of the $i^{th}$ brightest pixel value are stored in pointer array locations INDX(i) and INDY(i), where the index "i" runs from 1 to NOUT.

Synthesis of the first pixel cluster proceeds by designating INDX(1) and INDY(1) to be the X and Y coordinates of a nucleus of a first pixel cluster. In applications where the cross-sectional dimensions of the analyte particles within the sample are, for example, relatively circular, it will generally be desired to mirror this geometry by creating circular pixel clusters. In such instances the first nucleus is located at the center of a circle used to define the first pixel cluster. The radius for the first pixel cluster is determined by searching in eight directions (i.e., 45, 90, 135, 180, 225, 270 and 360 degrees) relative to the first nucleus for sorted pixels included within the image window. The object of this search is to determine an appropriate cluster radius in each of the eight directions, with these individual radii then being used to define the radius of the first pixel cluster.

More specifically, to determine the radius at 45 degrees the pixel having X coordinate INDX(1)+i and Y coordinate INDY(1)+i is examined to determine whether its coordinates are included in pointer arrays INDX and INDY. If so, the pixel being examined was deemed to be sufficiently bright to have been included within the image window. Consequently, the 45 degree radii of the first pixel cluster will be selected to at least include the examined pixel found to be within the image window. Assuming the pixel at the X,Y coordinate location INDX(1)+i, INDY(1)+i is included within the image window, it is then ascertained whether the coordinates of the next pixel in the 45 degree direction (i.e., the pixel having X,Y coordinates XINDX(1)+2, INDY(1)+2) are included within the pointer arrays INDX and INDY. If the coordinates of this second examined pixel are not included within INDX and INDY the 45 degree radii is set at a value of two. Similarly, if the coordinates of the first examined pixel were not found within INDX and INDY the 45 degree radii would be assigned a value of unity. The radii associated with the remaining seven direction vectors are next determined in a substantially identical manner. It would then be possible to compute a composite radius characteristic of the first pixel cluster by simply averaging these eight individual radii.

Alternatively, the largest two or three radii could be deleted prior to averaging in order to prevent the presence of a second pixel cluster having elements adjacent the periphery of the first cluster from making the radius of the first cluster inappropriately large. This scenario could arise, for example, when the separation between a pair of analyte particles within the sample is sufficiently small that the pixel clusters characterizing each are contiguous along at least one direction vector.

When the analyte particles within the sample are of non-circular cross-section the individual directional radii may be used to define a cluster periphery of arbitrary shape. Similarly, other non-circular (e.g., elliptical) contours may be favored by modifying the cluster boundary defined by the directional radii to more closely approximate a preferred shape.

As indicated by FIG. 7, those pixel elements sufficiently bright to be included within the image window and present within the circle defined by the first cluster nucleus and radius are grouped into the first pixel cluster. This step is implemented by scanning INDX and INDY to determine the coordinate locations therein encompassed by the area defined by the first pixel cluster. The entries in INDX and INDY so encompassed are designated as being within the first pixel cluster, and are then deleted from INDX and INDY. Further, the clustering program subtracts the number of pixel locations included within the first cluster from the number of pixel locations originally included within the image window. If this number is less than a predefined percentage (e.g., 99%) of the number of pixels included within the image window, then the clustering process terminates. Otherwise, formation of a second pixel cluster is commenced.

The nucleus of the second pixel cluster is determined by searching for the largest value remaining within the sorted list of pixel values included within the image window; that is, by searching for the brightest pixel not included within the first pixel cluster. The second pixel cluster is then formed in the same manner as was the first pixel cluster. Again, additional clusters are formed until the number of unclustered pixel values remaining on the sorted list of pixel values is less than a predefined percentage of the number originally present.

The inventive clustering process may be utilized in a variety of applications to spatially resolve and count discrete chemical entities. As noted above, one such application involves digital detection of analyte particles in which each particle is comprised of a molecule and fluorescent label. In similar fashion the number of chromosomes or partial chromosomes within a nucleus may be determined by selecting the pixel size to be small relative to the size of the fluorescent label. The label associated with individual chromosomes is thus distributed over a plurality of pixel regions, and clustering is required to facilitate counting of the number of chromosomes included within each nucleus.

The clustering process of the present invention may also be utilized in a scan mode to rapidly locate areas of interest within an image of a sample. In the scan mode image data is initially collected by interrogating the sample using a large pixel size. The clustering algorithm is then invoked in order to identify regions of interest through determination of the size and center of a number of pixel clusters. If it is then desired to synthesize higher-resolution images of the identified regions of interest, data may be collected from each such region using pixels of reduced area.

Laboratory Results

The clustering technique of the present invention was implemented using the apparatus of FIG. 2 in order to determine the number of fluorescent label beads present within samples of the following assay. The assay is comprised of magnetic capture beads coated with covalently attached $(dT)_{21}$ DNA oligomers, fluorescent label beads coated with a covalently attached sequence specific for human papilloma virus type 6 (HPV-6), DNA capture oligomers and analyte DNA molecules containing HPV-6 sequences.

In this example the magnetic capture beads are reacted with an excess of capture probe oligomers. The capture oligomers are 51 nucleotides in length. The 5' end of the capture probe is composed of a 30 base DNA sequence (nucleotides 810 through 840) of HPV-6 DNA. The 3' end of the capture probe is composed of $(dA)_{21}$. The $(dA)_{21}$ hybridizes to the $(dT)_{21}$ oligomers on the surface of the magnetic beads. Unhybridized capture probes were removed from the solution by magnetic concentration of the magnetic beads and removal and replacement of the supernatant solution.

Magnetic beads with hybridized capture probes were then mixed with varying quantities of HPV-6 DNA (analyte DNA) sequence. The analyte sequence used was an oligomer 42 nucleotides in length. Twenty-one nucleotides at the 5' end of the analyte sequence were complementary to 21 of the 30 nucleotides in the sequence of HPV-6 DNA on the capture probe. The 21 nucleotides at the 3' end of the analyte DNA were complementary to the DNA oligomers on the fluorescent label beads. The analyte DNA was hybridized to the capture probe on the magnetic beads.

The specific type and concentration of magnetic beads will be chosen so as to limit the concentration of analytes within each pixel region in order that the aggregate emitted signal from each region remains less than the upper detection threshold. One method of effecting this limiting is to select beads having only a single binding pair. Alternatively, a large number of beads relative to the number of analytes may be employed.

Fluorescent label beads were then hybridized to the analyte DNA on the magnetic capture beads. Unbound label beads were removed by repeated wash steps as described subsequently for the excess capture probe and unbound label DNA.

The specific methodology employed to prepare the samples involved adding twelve microliters of $1.5 \times 10^5$ magnetic beads per microliter of magnetic 2.8 um beads (Dynal, Inc., Great Neck, N.Y.) to 100 microliters of wash buffer (0.5M GuSCN, 0.04M Tris-HCl, 0.008M EDTA, 0.5% N-lauryl sarcosine, 0.5% BSA, pH 7.4). The bead suspension was mixed and the beads were concentrated magnetically, with the supernatant then being removed. Fifty microliters of wash buffer were added, and the beads were resuspended. Six micrograms of 51 nucleotide capture probe was added and the suspension was incubated at 37 degrees Centigrade for one hour. The beads were magnetically concentrated and the supernatant was again removed. One hundred microliters of fresh wash buffer was added, and the beads were resuspended. This wash procedure was repeated two additional times. The washed bead pellet was resuspended in 65 microliters of wash buffer and ten microliters of bead. suspension was transferred to each of six tubes. One microliter of 1 microgram per microliter of yeast tRNA was added to each tube.

One microliter of 100 pg/microliter analyte DNA and nine microliters of wash buffer were added to tube one. Ten microliters of 1 pg/microliter analyte DNA were added to tube two. Seven microliters of wash buffer and three microliters of 1 pg/microliter analyte DNA were added to tube 3. One microliter of 1 pg/microliter analyte DNA and nine microliters of wash buffer were added to tube 4. One microliter of 0.1 pg/microliter analyte DNA and nine microliters of wash buffer were added to tube 5. Ten microliters of wash buffer were added to tube 6.

The six samples were incubated at 37 degrees Centigrade for one hour. Three microliters of wash buffer and 2 microliters ($10^6$ beads/microliter) of 0.74 um fluorescent beads (YG Beads, Polysciences, Inc., Warrington, Pa.) were added to each of the samples. The incubation was continued for one additional hour at 37 degrees Centigrade. After incubation the capture beads were concentrated magnetically, and the supernatant containing unbound label beads was removed. The capture beads were resuspended in 50 microliters of wash buffer and mixed. The wash procedure was repeated 5 additional times. After the final wash, the beads were resuspended in 50 microliters of wash buffer. Placing a suitable quantity (e.g., five microliters) of each sample on a microscope slide would then allow observation to proceed in accordance with the inventive digital detection technique described herein.

It is evident from the above results and the description of the inventive clustering technique that accurate digital detection of analytes may be effected using fluorescence or other label providing for emitted light. In this way, one may detect a wide variety of analytes which may be present in samples at only extremely low concentrations.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A system for detecting the presence of a small number of analyte particles within a sample, said sample being divided into a multiplicity of distinct pixel regions where light emitted in each of said pixel regions is related to the amount of analyte in each of said pixel regions, comprising:

a plurality of pixel regions dimensioned such that the number of said analyte particles included within each of said pixel regions is less than a maximum detection threshold proportional to variation in optical responses emitted by said analyte particles;

means for measuring emitted signals from each of said pixel regions relative to an ambient noise threshold, wherein the emitted signal from each pixel region is proportional to said optical responses of analyte particles included therein; and data processing means for receiving said measurements and, based on said measurements, counting the number of analyte particles within each of said pixel regions in order to determine the number of said analyte particles within said sample.

2. The system of claim 1 wherein said data processing means includes means for dividing each of said measurements by a value corresponding to a magnitude of one of said optical responses;

whereby the integer nearest the result of each division corresponds to the number of said analyte particles within one of said pixel regions.

3. The system of claim 1 further including means for illuminating each pixel region, wherein said measuring means includes wavelength isolation means for separating said optical responses from light provided by said illuminating means.

4. The system of claim 3 wherein said means for illuminating includes laser beam means for providing a focused illumination beam at optical wavelengths primarily confined to a first spectral range.

5. The system of claim 4 wherein said means for wavelength isolation includes an optical filter tuned to reject light included within said first spectral range.

6. The system of claim 5 wherein each of said pixel regions are of substantially equivalent area and are arranged contiguously within said sample, and wherein said illumination means further includes raster scanning means for sequentially illuminating each of said pixel regions with said focused illumination beam for a predefined time interval.

7. The system of claim 6 wherein said means for collecting includes a photodetector for generating a detection signal in response to illumination by photons within each of said optical responses.

8. The system of claim 7 wherein said measuring means includes a detector circuit addressed by said detection signal for counting the number of photons emitted from each of said pixel regions, said measuring means further including an electronic memory for storing said pixel counts.

9. The system of claim 1 wherein said data processing means includes means for generating an array of data values wherein each of said data values corresponds to said measured emitted signal from one of said pixel regions.

10. The system of claim 9 wherein said data processing means further includes:
   means for calculating a background noise level based on said data values, and
   means for comparing each of said data values to said background noise level in order to determine whether at least one of said analytes is included within the pixel region associated therewith.

11. The system of claim 10 wherein said data processing means further includes:
   means for calculating a background noise level based on said data values,
   means for arranging in descending order a set of said data values which exceed said noise level by an interest threshold, and
   selecting the largest of said arranged set of data values whereby the pixel region associated with said selected data value becomes a nucleus of a first of said pixel clusters.

12. The system of claim 11 wherein said data processing means further includes:
   means for identifying data values within said arranged set of data values associated with pixel regions proximate said nucleus, and
   means for grouping said identified data values into said first pixel cluster.

13. The system of claim 12 wherein said data processing means further includes means for designating the largest of said arranged data values associated with a pixel region not included within said first cluster as a nucleus of a second of said pixel clusters.

14. A system for digitally detecting the presence of analyte particles within a sample in which each analyte particle is disposed to emit an optical response upon being illuminated in a predetermined manner, wherein the number of said analyte particles is less than a maximum detection threshold proportional to variability in said optical responses, comprising:
   means for illuminating said sample in order to induce said analyte particles to emit said optical responses;
   means for collecting an emitted signal comprised of said optical responses; and
   means for measuring said collected emitted signal and for comparing said measured emitted signal with a detection threshold in order to count the number of analyte particles within said sample.

15. The system of claim 14 wherein said means for measuring said emitted signal includes means for dividing said measured emitted signal by a value corresponding to a magnitude of said optical responses;
   whereby the integer nearest said divided measurement corresponds to the number of analyte particles within said sample.

16. The system of claim 15 wherein
said means for illuminating produces illuminating light at frequencies distinct from optical frequencies associated with said optical responses, and wherein said means for collecting includes means for wavelength isolation from said illuminating light said collected optical responses.

17. The system of claim 16 wherein said means for illuminating includes laser beam means for providing a focused illumination beam at wavelengths confined to a first spectral range.

18. The system of claim 17 wherein said wavelength isolation means includes an optical filter tuned to reject light included within said first spectral range.

19. A method for detecting the presence of a small number of analyte particles within a sample, said sample being divided into a multiplicity of distinct pixel regions where light emitted in each of said pixel regions is related to the amount of analyte in each of said pixel regions, comprising the steps of:
   dimensioning each of said pixel regions such that the number of said analyte particles included within each of said pixel regions is less than a maximum detection threshold proportional to variation in optical responses emitted by said analyte particles;
   measuring emitted signals from each of said pixel regions relative to an ambient noise threshold, wherein the emitted signal from each pixel region is proportional to said optical responses of analyte particles included therein; and
   counting, based on said measurements, the number of analyte particles within each of said pixel regions in order to determine the number of said analyte particles within said sample.

20. The method of claim 19 further including the step of dividing each of said measurements by a value corresponding to a magnitude of said optical responses;
   whereby the integer nearest each of said divided measurements corresponds to the number of said analyte particles within one of said pixel regions.

21. The method of claim 19 further including the step of illuminating each of said pixel regions with illuminating light, wherein:
   said step of illuminating includes the step of producing illuminating light at frequencies distinct from optical frequencies associated with said optical responses, and
   said step of measuring includes the step of filtering said optical responses from said illuminating light.

22. The method of claim 21 wherein said step of illuminating further includes the step of providing a focused illumination beam at wavelengths primarily confined to a first spectral range.

23. The method of claim 19 further including the step of preparing said sample of analyte particles wherein said step of preparing includes the steps of:
   binding analytes to a surface by means of a specific binding pair member;
   forming analyte particles by contacting said analytes with a plurality of flurophor labels disposed to combine with said analyte particles in a predetermined manner; and
   removing said flurophor labels not specifically bound to an analyte from the vicinity of said surface.

24. The method of claim 23 wherein said step of attaching includes the step of binding a binding member complementary to said analyte upon said surface.

25. The method of claim 24 wherein said binding member comprises an antibody specific to said analyte.

26. The method of claim 23 wherein each of said analytes is bound to a magnetic bead, and wherein said step of attaching includes the step of applying a magnetic field in the vicinity of said surface so as to induce contact between said analytes and said surface.

27. The method of claim 19 wherein said step of counting further includes the step of generating an array of data values wherein each of said data values corresponds to said measured emitted signal from one of said pixel regions.

28. The method of claim 27 wherein said step of counting further includes the steps of:

calculating a background noise level based on said data values, and comparing each of said data values to said background noise level in order to determine whether at least one of said analyte particles is included within the pixel region associated therewith.

29. The method of claim 28 wherein said step of counting further includes the steps of:

calculating a background noise level based on said data values, arranging in descending order a set of said data values which exceed said noise level by an interest threshold, and selecting the largest of said arranged set of data values whereby the pixel region associated with said selected data value becomes a nucleus of a first of said pixel clusters.

30. The method of claim 29 wherein said step of counting further includes the steps of:

identifying data values within said arranged set of data values associated with pixel regions proximate said nucleus, and grouping said identified data values into said first pixel cluster.

31. The method of claim 30 wherein said step of counting further includes the step of designating the largest of said arranged data values associated with a pixel region not included within said first cluster as a nucleus of a second of said pixel clusters.

32. A method for digitally detecting the presence of molecular analyte particles within a sample in which each analyte particle is disposed to emit an optical response upon being illuminated in a predetermined manner, wherein the concentration of said analyte particles is less than a maximum detection threshold proportional to variability in said optical responses, comprising the steps of:

illuminating said sample in order to induce said analyte particles to emit said optical responses;

collecting an emitted signal comprised of said optical responses; and measuring said collected emitted signal and comparing said measured emitted signal with a detection threshold in order to count the number of analyte particles within said sample.

33. The method of claim 32 wherein said step of measuring said collected emitted signal includes the step of dividing said measurement by a value corresponding to one of said optical responses;

whereby said divided measurement corresponds to the number of analyte particles within said sample.

* * * * *